United States Patent
Ghose et al.

(10) Patent No.: US 10,726,110 B2
(45) Date of Patent: Jul. 28, 2020

(54) WATERMARKING FOR DATA SECURITY IN BIOINFORMATIC SEQUENCE ANALYSIS

(71) Applicant: Seven Bridges Genomics, Inc., Cambridge, MA (US)

(72) Inventors: Kaushik Ghose, Malden, MA (US); Deniz Kural, Somerville, MA (US)

(73) Assignee: Seven Bridges Genomics, Inc., Cambridge, MA (US)

( * ) Notice: Subject to any disclaimer, the term of this patent is extended or adjusted under 35 U.S.C. 154(b) by 247 days.

(21) Appl. No.: 15/907,835

(22) Filed: Feb. 28, 2018

(65) Prior Publication Data

US 2018/0253536 A1    Sep. 6, 2018

Related U.S. Application Data

(60) Provisional application No. 62/465,454, filed on Mar. 1, 2017.

(51) Int. Cl.
| | |
|---|---|
| *G06F 21/16* | (2013.01) |
| *G16B 30/10* | (2019.01) |
| *G06F 16/901* | (2019.01) |
| *G16B 5/00* | (2019.01) |
| *G16B 30/00* | (2019.01) |
| *G16B 50/00* | (2019.01) |
| *G16B 50/40* | (2019.01) |

(52) U.S. Cl.
CPC .......... *G06F 21/16* (2013.01); *G06F 16/9024* (2019.01); *G16B 5/00* (2019.02); *G16B 30/00* (2019.02); *G16B 50/00* (2019.02); *G16B 50/40* (2019.02); *G16B 30/10* (2019.02)

(58) Field of Classification Search
CPC ........ G06F 21/10; G06F 21/16; G06F 16/901; G06F 16/9024
See application file for complete search history.

(56) References Cited

U.S. PATENT DOCUMENTS

| | | |
|---|---|---|
| 5,511,158 A | 4/1996 | Sims |
| 5,701,256 A | 12/1997 | Marr et al. |
| 6,054,278 A | 4/2000 | Dodge et al. |
| 6,223,128 B1 | 4/2001 | Allex et al. |

(Continued)

FOREIGN PATENT DOCUMENTS

| | | |
|---|---|---|
| WO | 2012096579 A3 | 7/2012 |
| WO | 2012098515 A1 | 7/2012 |

(Continued)

OTHER PUBLICATIONS

Dominik Heider and Angelika Barnekow, DNA watermarks: A proof of concept, Apr. 21, 2008, BMC Molecular Biology 2008, 9:40 doi:10.1186/1471-2199-9-40 (Year: 2008).*

(Continued)

*Primary Examiner* — Khang Do
(74) *Attorney, Agent, or Firm* — Morgan, Lewis & Bockius LLP

(57) ABSTRACT

Embodiments of the invention protect information stored in graph-based sequence references by "watermarking" the graph with uniquely identifiable information. The watermark identifies the graph or version thereof in a detectable but nonintrusive manner. In one embodiment, insertions and/or deletions are introduced into regions of the graph.

17 Claims, 2 Drawing Sheets

Specification includes a Sequence Listing.

(56) References Cited

U.S. PATENT DOCUMENTS

| | | | |
|---|---|---|---|
| 6,625,780 B1* | 9/2003 | Charbon | G06F 30/30 |
| | | | 716/103 |
| 7,577,554 B2 | 8/2009 | Lystad et al. | |
| 7,580,918 B2 | 8/2009 | Chang et al. | |
| 7,809,509 B2 | 10/2010 | Milosavljevic | |
| 7,885,840 B2 | 2/2011 | Sadiq et al. | |
| 7,917,302 B2 | 3/2011 | Rognes | |
| 8,209,130 B1 | 6/2012 | Kennedy et al. | |
| 8,340,914 B2 | 12/2012 | Gatewood et al. | |
| 8,370,079 B2 | 2/2013 | Sorenson et al. | |
| 8,639,847 B2 | 1/2014 | Blaszczak et al. | |
| 9,063,914 B2 | 6/2015 | Kural et al. | |
| 9,092,402 B2 | 7/2015 | Kural et al. | |
| 9,116,866 B2 | 8/2015 | Kural | |
| 9,390,226 B2 | 7/2016 | Kural | |
| 9,817,944 B2 | 11/2017 | Kural | |
| 2002/0037521 A1* | 3/2002 | Kashima | C12N 15/10 |
| | | | 435/6.13 |
| 2004/0023209 A1 | 2/2004 | Jonasson | |
| 2005/0089906 A1 | 4/2005 | Furuta et al. | |
| 2006/0292611 A1 | 12/2006 | Berka et al. | |
| 2007/0166707 A1 | 7/2007 | Schadt et al. | |
| 2008/0077607 A1 | 3/2008 | Gatawood et al. | |
| 2008/0294403 A1 | 11/2008 | Zhu et al. | |
| 2009/0119313 A1 | 5/2009 | Pearce | |
| 2009/0164135 A1 | 6/2009 | Brodzik et al. | |
| 2009/0275086 A1* | 11/2009 | Gibson | C12N 15/81 |
| | | | 435/91.1 |
| 2009/0300781 A1 | 12/2009 | Bancroft et al. | |
| 2010/0041048 A1 | 2/2010 | Diehl et al. | |
| 2010/0169026 A1 | 7/2010 | Sorenson et al. | |
| 2011/0004413 A1 | 1/2011 | Carnevall et al. | |
| 2011/0053273 A1* | 3/2011 | Benders | C12N 15/10 |
| | | | 435/455 |
| 2011/0098193 A1 | 4/2011 | Kingsmore et al. | |
| 2011/0269119 A1* | 11/2011 | Hutchison | C12Q 1/6806 |
| | | | 435/6.1 |
| 2012/0041727 A1 | 2/2012 | Mishra et al. | |
| 2012/0045771 A1 | 2/2012 | Beier et al. | |
| 2012/0239706 A1 | 9/2012 | Steinfadt | |
| 2012/0270321 A1* | 10/2012 | Dormitzer | A61K 39/145 |
| | | | 435/455 |
| 2012/0330566 A1 | 12/2012 | Chaisson | |
| 2013/0059738 A1 | 3/2013 | Leamon et al. | |
| 2013/0059740 A1 | 3/2013 | Drmanac et al. | |
| 2013/0073214 A1 | 3/2013 | Hyland et al. | |
| 2013/0124100 A1 | 5/2013 | Drmanac et al. | |
| 2013/0289099 A1 | 10/2013 | Goff et al. | |
| 2013/0311106 A1 | 11/2013 | White et al. | |
| 2014/0025312 A1 | 1/2014 | Chin et al. | |
| 2014/0051588 A9 | 2/2014 | Drmanac et al. | |
| 2014/0066317 A1 | 3/2014 | Talasaz | |
| 2014/0136120 A1 | 5/2014 | Colwell et al. | |
| 2014/0200147 A1 | 7/2014 | Bartha et al. | |
| 2014/0274806 A1* | 9/2014 | O'Hagan | C12N 7/00 |
| | | | 506/17 |
| 2014/0278590 A1 | 9/2014 | Abbassi et al. | |
| 2014/0280360 A1 | 9/2014 | Webber et al. | |
| 2014/0323320 A1 | 10/2014 | Jia et al. | |
| 2015/0056613 A1 | 2/2015 | Kural | |
| 2015/0057946 A1* | 2/2015 | Kural | G16B 30/00 |
| | | | 702/20 |
| 2015/0063698 A1* | 3/2015 | Adini | G06K 9/18 |
| | | | 382/176 |
| 2015/0094212 A1 | 4/2015 | Gottimukkala et al. | |
| 2015/0110754 A1 | 4/2015 | Bai et al. | |
| 2015/0112602 A1 | 4/2015 | Kural et al. | |
| 2015/0112658 A1 | 4/2015 | Kural et al. | |
| 2015/0197815 A1 | 7/2015 | Kural | |
| 2015/0199472 A1 | 7/2015 | Kural | |
| 2015/0199473 A1 | 7/2015 | Kural | |
| 2015/0199474 A1 | 7/2015 | Kural | |
| 2015/0199475 A1 | 7/2015 | Kural | |
| 2015/0227685 A1 | 8/2015 | Kural | |
| 2015/0293994 A1 | 10/2015 | Kelly | |
| 2015/0302145 A1 | 10/2015 | Kural et al. | |
| 2015/0310167 A1 | 10/2015 | Kural et al. | |
| 2015/0344970 A1 | 12/2015 | Vogelstein et al. | |
| 2015/0347678 A1 | 12/2015 | Kural | |
| 2015/0356147 A1 | 12/2015 | Mishra et al. | |
| 2016/0259880 A1 | 9/2016 | Semenyuk | |
| 2016/0306921 A1 | 10/2016 | Kural | |
| 2016/0364523 A1 | 12/2016 | Locke et al. | |
| 2016/0365979 A1* | 12/2016 | Mai | H04L 63/0876 |
| 2017/0058320 A1 | 3/2017 | Locke et al. | |
| 2017/0058341 A1 | 3/2017 | Locke et al. | |
| 2017/0058365 A1 | 3/2017 | Locke et al. | |
| 2017/0198351 A1 | 7/2017 | Lee et al. | |
| 2017/0199959 A1 | 7/2017 | Locke | |
| 2017/0199960 A1 | 7/2017 | Ghose et al. | |
| 2017/0242958 A1 | 8/2017 | Brown | |
| 2018/0340218 A1* | 11/2018 | Abudayyeh | C12P 19/34 |
| 2019/0087927 A1* | 3/2019 | Dewitt | G06T 1/0035 |
| 2020/0063164 A1* | 2/2020 | Fredens | C12N 15/902 |

FOREIGN PATENT DOCUMENTS

| | | |
|---|---|---|
| WO | 2012142531 A2 | 10/2012 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Agarwal, 2013, SINNET: Social interaction Network Extractor from Text, Proc IJCNLP 33-36.

Aguiar, 2012, HapCompass: A fast cycle basis algorithm for accurate haplotype assembly of sequence data, J Comp Biol 19(6):577-590.

Aguiar, 2013, Haplotype assembly in polyploid genomes and identical by descent shared tracts, BioInformatics 29(13): i352-i360.

Airoldi, 2008, Mixed membership stochastic blockmodels, JMLR 9:1981-2014.

Albers, 2011, Dindel: Accurate indel calls from short-read data, Genome Research 21:961-973.

Alioto et al., A comprehensive assessment of somatic mutation detection in cancer using whole-genome sequencing, Nature Communications, Dec. 9, 2015.

Altera, 2007, Implementation of the Smith-Waterman algorithm on reconfigurable supercomputing platform, White Paper ver 1.0 (18 pages).

Altschul, 1986, Optimal Sequence Alignment Using Affine Gap Costs, Bull Math Biol 48(5/6):603-616.

Bansal, 2008, An MCMC algorithm for haplotype assembly from whole-genome sequence data, Genome Res 18:1336-1346.

Bao, 2013, BRANCH: boosting RNA-Seq assemblies with partial or related genomic sequences, Bioinformatics 29(10):1250-1259.

Barbieri, 2013, Exome sequencing identifies recurrent SPOP, FOXA1 and MED12 mutations in prostate cancer, Nature Genetics 44:6 685-689.

Beerenwinkel, 2007, Conjunctive Bayesian Networks, Bernoulli 13(4), 893-909.

Berlin, 2014, Assembling large genomes with single-molecule sequencing and locality sensitive hashing, bioRxiv preprint (35 pages); retrieved from the internet on Jan. 29, 2015, at.

Bertrand, 2009, Genetic map refinement using a comparative genornic approach, J Comp Biol 16(10):1475-1486.

(56) References Cited

OTHER PUBLICATIONS

Black, 2005, A simple answer for a splicing conundrum, PNAS 102:4927-8.
Boyer, 1977, A Fast String Searching Algorithm, Comm ACM 20(10):762-772.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Chang, 2005, The application of alternative splicing graphs in quantitative analysis of alternative splicing form from EST database, Int J Comp Appl Tech 22(1):14.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Compeau, 2011, How to apply de Bruijn graphs to genorne assembly, Nat Biotech 29(11):987-991.
Craig, 1990, Ordering of cosmid clones covering the Herpes simplex virus type 1 (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
DePristo, 2011, A framework for variation discovery and genotyping using next-generation DNA sequencing data, Nat Gen 43:491-498.
Duan et al., Optimizing de novo common wheat transcriptome assembly using short-read RNA-Seq data. (2012) pp. 1-12, vol. 13, BMC Genomics.
Dudley, 2009, A quick guide for developing effective bioinformatics programming skills, PLoS Comput Biol 5(12): e1000589.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SNP map, BMC Genomics 12(1):407 (and whole document).
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Farrar, 2007, Striped Smith-Waterman speeds database searches six times over other SIMD implementations, Bioinformatics 23(2):156-161.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2013, Genome-guided transcriptome assembly in the age of next-aeneration sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp, 531-537.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Grasso, 2004, Combining partial order alignment and progressive multiple sequence alignment increases alignment speed and scalability to very large alignment problems, Bioinformatics 20(10):1546-1556.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Homer, 2010, Improved variant discovery through local re-alignment of short-read next generation sequencing data using SRMA, Genome Biol 11(10):R99.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hutchinson, 2014, Allele-specific methylation occurs at genetic variants associated with complex diseases, PLoS One 9(6):e98464.
International Search Report and Written Opinion dated Aug. 31, 2017, for International Application No. PCT/US2017/018830 with International Filing Date Feb. 22, 2017, (11 pages).
International Search Report and Written Opinion dated Mar. 31, 2015 for International Application No. PCT/US2015/010604 filed Jan. 8, 2015 (13 pages).
International Search Report and Written Opinion dated Apr. 19, 2017 for International Patent Application No. PCT/US2017/012015, (14 Pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for International Patent Application No. PCT/US16/57324 with International Filing Date Oct. 17, 2016, (7 pages).
International Search Report and Written Opinion dated Mar. 19, 2015, for International Application No. PCT/US2014/061162 with International Filing Date Oct. 17, 2014, (12 pages).
International Search Report and Written Opinion dated May 11, 2015, for International Patent Application No. PCT/US2015/015375 with International Filing Date Feb. 11, 2015, (12 pages).
International Search Report and Written Opinion dated May 5, 2016, for International Patent Application No. PCT/US2016/020899, wiht International Filing Date Mar. 4, 2016, (12 pages).
International Search Report and Written Opinion dated Apr. 7, 2017, for International Patent Application No. PCT/US17/13329, filed Jan. 13, 2017, (9 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014, (22 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, PCT/US2014/060690 (11 pages).

(56) References Cited

OTHER PUBLICATIONS

International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016, (14 pages).
International Search Report and Written Opinion dated Sep. 7, 2016, for International Application No. PCT/US2016/036873 with International filing date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptome data, BMC Genomics 11:571.
Kurtz, 2004, Versatile and open software for comparing large genomes, Genome Biol 5:R12.
Lam, 2008, Compressed indexing and local alignment of DNA, Bioinforrnatics 24(6):791-97.
Langmead, 2009, Ultrafast and memory-efficient alignment of short DNA sequences to the human genome, Genome Biol 10:R25.
Larkin, 2007, Clustal Wand Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2009, Fast and accurate short read alignment with Burrows-Wheeler Transform. Bioinformatics 25:1754-60.
Li, 2010, A survey of sequence alignment algorithms for next-generation sequencing, Briefings in Bionformatics 11(5):473-483.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Lupski, 2005, Genomic disorders: Molecular mechanisms for rearrangements and conveyed phenotypes, PLoS Genetics 1(6):e49.
Ma, 2010, Multiple genome alignment based on longest path in directed acyclic graphs, Int J Bioinformatics 6(4):366-683.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the Internet on Jun. 3, 2016, at.
Marth et al., 1999—A general approach to single-nucleotide polymorphism discovery, pp. 452-456, vol. 23, Nature Genetics.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Mount, 2001, Multiple Sequence Alignment, Bioinformatics, 2001, Cold Spring Harbor Laboratory Press, Cold Spring Harbor, New York, pp. 139-204.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Nagarajan, 2013, Sequence assembly demystified, Nat Rev 14:157-167.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Newman, 2013, Community detection and graph portioning, Europhys Lett 103(2):28003, arXiv:1305.4974v1.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Oshiack, 2010, From RNA-seq reads to differential expression results. Genome Bio 11:220.
Parks, 2015, Detecting non-allelic homologous recombination from high-throughput sequencing data, Genome Biol 16:17.
Peixoto, 2014, Efficient Monte Carlo and greedy heuristic for the inference of stochastic block models, Phys. Rev. E 89, 012804.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.

(56) References Cited

OTHER PUBLICATIONS

Ronquist, 2012, MrBayes 3,2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 2012, Multiple insert size paired-end sequencing for deconvolution of complex transcriptions, RNA Bio 9(5) 596-609.
Sosa, 2012, Next-Generation Sequencing of Human Mitochondrial Reference Genomes Uncovers High Heteroplasmy Frequency, PLoS One 8(10):e1002737.
Sturgeon, RCDA: A highly sensitive and specific alternatively spliced transcript assembly tool featuring upstream consecutive exon structures, Genomics, Dec. 2012, 100(6): 357-362.
Subramanian, 2006, DIALIGN-TX: greedy and progessive approaches for seament-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the Internet on Jun. 3, 2016, at.
Szaikowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Wang, 2009, RNA-Seq: a revolutionary tool for transcriptomics, Nat Rev Genet 10(1):57-63.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yanovsky, 2008, Read mapping algorithms for single molecule sequencing data, Proc 8th Int Workshop Alg Bioinformatics 5251:38-49.
Yu, 2010, The construction of a tetraploid cotton genome wide comprehensive reference map, Genomics 95:230-240.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.

* cited by examiner

SEQUENCE LISTING

```
<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
gatgctcgga agctaggact gt                                          22

<210> SEQ ID NO 2
<211> LENGTH: 22
```

```
<212> TYPE: DNA
<213> ORGANISM: Homo sapiens

<400> SEQUENCE: 2
gatgctcgga acctaggact gt                                             22
```

WATERMARKING FOR DATA SECURITY IN BIOINFORMATIC SEQUENCE ANALYSIS

CROSS-REFERENCE TO RELATED APPLICATION

This application claims priority to and the benefit of, and incorporates herein by reference in its entirety, U.S. Provisional Patent Application No. 62/465,454, filed on Mar. 1, 2017 and incorporated herein by reference in their entireties.

TECHNICAL FIELD

Embodiments of the present invention relate generally to workflow processing of bioinformatic data, e.g., data obtained by sequencing a nucleic acid.

SEQUENCE LISTING

The instant application contains a Sequence Listing which has been submitted in ASCII format via EFS-Web and is hereby incorporated by reference in its entirety. Said ASCII copy, created on May 11, 2018, is named SBG-067_ST25.txt and is 571 bytes in size.

BACKGROUND

The science of bioinformatics applies sophisticated analytic techniques to biological data, such as genome sequences, to better understand the underlying biology. "Next generation" sequencing systems perform chemical analysis of a sample containing nucleic acid and generate many sequence "reads," i.e., short nucleic-acid segments typically less than 1000 base pairs (bp) in length. Overlapping reads are aligned to a reference sequence (such as a genome) to reveal important genetic or structural information (e.g., biomarkers for disease). Ultimately, the goal of sequence alignment is to combine the set of nucleic acid reads produced by the sequencer to achieve a longer read (a "contig") or even the entire genome of the sample source. Because the sequence data from next-generation sequencers often comprises millions of shorter sequences that together represent the totality of the target sequence, aligning the reads is complex and computationally expensive. Systems that perform this type of alignment may represent sequences as graph data structures (e.g., directed acyclic graphs); a representative system is described in U.S. Pat. No. 9,390,226, the entire disclosure of which is hereby incorporated by reference.

The graph-based references may be quite valuable, representing the results of multiple sequencing efforts that have been analyzed to identify variants—e.g., single-nucleotide polymorphisms (SNPs), structural variants, insertions and deletions—among different individuals of the same species. Candidate sequences, which may be very short "k-mers" (sequences of length k bp, where k is generally less than 100 and often less than 20) or longer reads, are analyzed against a reference sequence using an alignment tool, which determines the degree of similarity between the candidate sequence and the reference sequence over the entirety of the latter—that is, the alignment tool finds the best match between an input segment and the reference segment wherever this match occurs and reports a score indicating the quality of the match.

Although service bureaus that accept candidate sequences and perform alignments against proprietary reference sequences can easily maintain their physical security, these sequences nonetheless remain vulnerable to illicit reconstruction by intruders who may, for example, submit candidate sequences structured so that the resulting alignment provides information about the reference sequence graph. In sufficient quantity, such information can permit reconstruction or all or part of the graph. If a reference graph is made available publicly (e.g., for use with a proprietary alignment tool), those with access may simply copy or modify the graph in violation of contractual or other legal obligations.

Generating graph-based genome references is a time- and resource-intensive process. Graph genome content is not easily protectable, particularly when results generated by querying the graph are shared. Security methods are required to protect ownership of this shared resource and to dissuade malicious extraction of the data stored within.

SUMMARY

In various embodiments, the invention pertains to systems and methods for protecting information stored in private references that are available to be queried—e.g., graph-based sequence references that users query through an interface, providing short reads to obtain the results of an alignment against the reference sequence—by "watermarking" the graph with uniquely identifiable information. The watermark identifies the graph (or a particular version of the graph, if watermarks are changed from version to version) in a manner that is detectable yet does not compromise the results returned to users. Watermarking as described herein is useful against theft by reconstruction or illicit slavish copying of all or a portion of a reference graph.

Accordingly, in a first aspect, the present invention pertains to a system for modifying a DNA sequence corresponding to a genome or portion thereof and represented as a graph. In various embodiments, the system comprises a memory partition for storing the sequence; and a watermarking module for modifying the sequence by introducing a watermarking artifact therein, the watermarking artifact comprising at least one of (a) a plurality of variants not found in natural genomic DNA, (b) a variant introduced in a repeat sequence other than the first of a plurality of repeat sequences in a repetitive region, (c) at least one sequence no longer than 30 bp not found in natural genomic DNA, or (d) metadata associated with variants in the reference graph.

The watermarking artifact may, for example, be introduced in a region within 100 bp, 250 bp, or 500 bp of centromere DNA. The graph may include multiple paths at least one of which corresponds to a natural DNA sequence and another of which includes at least one variant not found in natural genomic DNA. For example, a variant not found in natural genomic DNA may be a private variant found only in a single individual—e.g., a variant identified from a trio experiment. The variant(s) may be in a k-mer with k ranging from 15-30 bp. Metadata may include variant allele frequency information.

In some embodiments, a watermarking artifact comprises a frameshift in an essential gene and/or encodes an alternative protein sequence. For example, the alternative protein sequence may spell out a word in a language (e.g., English). A variant introduced in a repeat sequence may be or comprise a variant introduced in the middle of a repeat sequence.

In another aspect, the invention pertains to a method of watermarking a DNA sequence corresponding to a genome or portion thereof and represented as a graph and stored as a data structure in a computer memory. In various embodiments, the method comprises modifying the memory contents corresponding to the sequence by introducing a watermarking artifact therein, where the watermarking artifact comprises at least one of (a) a plurality of variants not found in natural genomic DNA, (b) a variant introduced in a repeat sequence other than the first of a plurality of repeat sequences in a repetitive region, (c) at least one sequence no longer than 30 bp not found in natural genomic DNA, or (d) metadata associated with variants in the reference graph.

In still another aspect, the invention relates to a watermarked, computer-searchable data structure representing a DNA sequence corresponding to a genome or portion thereof, the data structure having the form of a graph and comprising a watermarking artifact therein, the watermarking artifact comprising at least one of (a) a plurality of insertions and deletions not found in natural genomic DNA, (b) a variant introduced in a repeat sequence other than the first of a plurality of repeat sequences in a repetitive region, (c) at least one sequence no longer than 30 bp not found in natural genomic DNA, or (d) metadata associated with variants in the reference graph.

Yet another aspect of the invention pertains to a method of detecting an attack on a proprietary graph representation of a genome or portion thereof, where the graph includes multiple paths and, along at least one path, one or more watermarks each corresponding to at least one variant not found in natural genomic DNA. In various embodiments, the method comprises the steps of receiving, from a user, a set of candidate DNA sequences for alignment with the graph representation; detecting whether a plurality of the set of candidate DNA sequences aligns with a path containing a watermark, and if so, rejecting the set of candidate DNA sequences (or portion thereof); if not, however, an alignment may be performed for some or all of the candidate sequences against a path of the graph not containing a watermark and the results of the alignment returned to the user.

In some embodiments, the set of candidate DNA sequences may be rejected if it aligns to multiple watermark sequences. In some embodiments, the set of candidate DNA sequences may be rejected if at least 25% of the candidate sequences overlapping a particular watermark sequence align to the particular watermark sequence. The watermark may, for example, be a k-mer with k ranging from 15-30 bp.

The term "substantially" or "approximately" means±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 1:
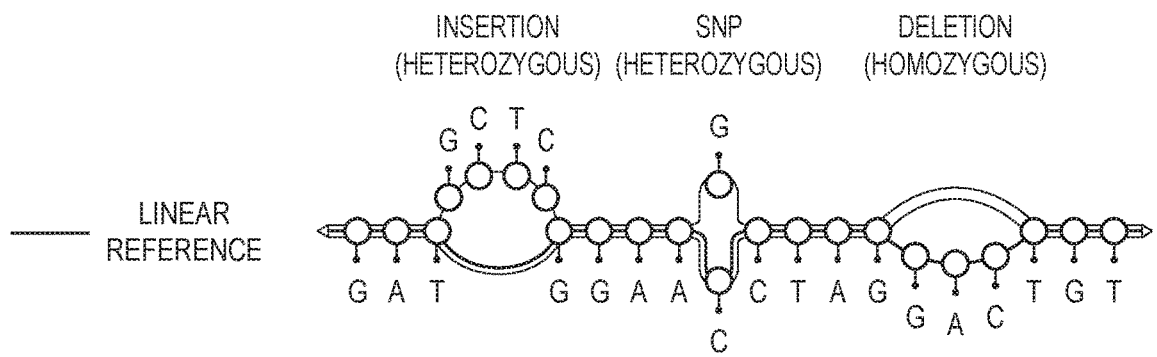
FIG. 1 illustrates a representative genomic reference graph of SEQ ID NOs: 1 and 2.

Embodiments of the invention protect information stored in graph-based sequence references by "watermarking" the graph with uniquely identifiable information. The watermark identifies the graph or version thereof in a detectable but nonintrusive manner. In one embodiment, insertions and/or deletions are introduced into regions of the graph. This may be understood with reference to FIG. 1, which illustrates a representative genomic reference graph. The reference graph reflects variants observed in the population, which are added to a reference sequence to construct a directed acyclic graph comprised of edges and vertices as illustrated. Variants—SNPs, insertions, deletions, and large structural variants—are represented by alternate branches in the graph. Branches can originate from the backbone sequence or from within a known variant (e.g., a SNP inside an insertion). A path through the graph represents a genome or a portion thereof. A non-natural insertion or deletion— i.e., one not observed in an actual population—can serve as a detectable signature in the graph reference used to identify the unique contents as belonging to a party. This signature will not affect the results of querying the graph; legitimate candidate sequences will not align to its path and thus it will never be returned to a user submitting valid sequence reads. For example, in one embodiment, an introduced deletion results in a one-bp frameshift in an essential gene. As shown in FIG. 1, deletions can be encoded by a single edge (or vertex) and are easily added to a reference graph. In the event that an arbitrary deletion does not exist in nature, sample reads will not align to it. Insertions can accomplish the same objective, and in fact can add conspicuous elements to the graph if desired; for example, the insertion AGCGAAGTAGAGAAT encodes the amino-acid sequence SEVEN. Ordinarily, of course, conspicuousness is to be avoided so the watermark is not easily detected. In various embodiments, a combination of insertions and deletions is employed since an attacker may test for both.

Figure 2:
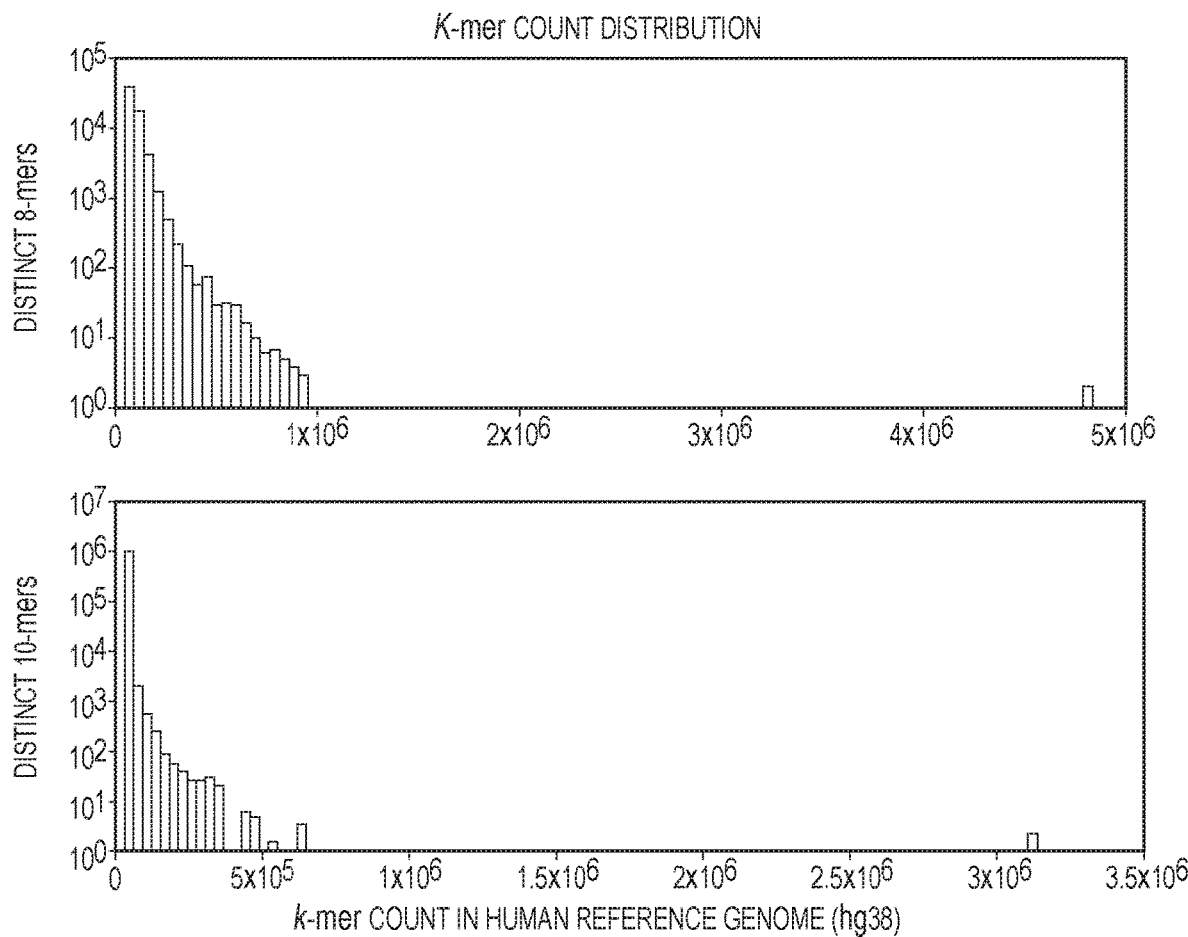
FIG. 2 graphically illustrates k-mer frequency distributions in a human reference genome.

For example, there exists some k that is relatively small yet many k-mers exist that do not naturally appear in the genome. As the length of k increases, so does the number of unique k-mers. As shown in FIG. 2, for example, most k-mers of length 8 are common in the human genome; increasing the length to 10 results in many more k-mers that are relatively unique. Accordingly, it is possible to generate k-mers of between 10-30 bp, confirm their absence in the human reference genome, and then include them as insertions in a few regions. Typically, the upper practical limit for k is around 30, as there are very few instances of large scale insertions in most variant sets; an insertion larger than 100 bp, for example, might be conspicuous. It is not necessary for the k-mer never to occur naturally in the genome if some degree of detection uncertainty is tolerable, e.g., if this watermark is combined with one or more others also subject to a degree of uncertainty.

Of course, if the graph is used to detect alignments of submitted candidate sequences to a natural genome, the watermark cannot interfere with the integrity of the alignment process. This may be avoided by providing multiple paths through the graph as suggested in the above illustration, including both unmodified paths corresponding to variations of the natural sequence and at least one path containing the watermark. Any candidate sequence mapping to a legitimate sequence will align with one of the unmodified paths.

In some cases, the information represented in a reference graph can be sufficiently unique that its appearance elsewhere represents strong evidence of copying. For example, some graphs encode allele frequency with variants, reflecting their prevalence within a population. These pieces of information may not be widely available, particularly together, and their simultaneous appearance in another graph—particularly if present in only part of the graph—suggests copying.

Another strategy exploits the fact that repeat regions cause ambiguities in alignment, i.e., it is common for reads to pile up around the first repeat in a sequence of repeats because aligners tend to favor a first match. Thus, a variant in the middle of a repeat region is unlikely to be detected and can serve as a unique watermark because a read aligned to an artificial variant in the $n^{th}$ repeat (for n>1) is likely to have been corrupted during the sequencing process, or perhaps was maliciously constructed. For example, a repetitive region (e.g., 10-15 repeats, about 1 kbp in total length) in a reference genome is unlikely to have a repeat variant in the middle because it is hard to accurately sequence these regions, identify the variant, and then put it in a dataset. As a result, a graph that includes a variant in the middle of a large known repeat like this would be suspect.

Centromere DNA is one species of noncoding DNA. Unlike genes coding for proteins, noncoding DNA does not express a triplet code that is translated into specific amino acids. Instead, noncoding DNA may provide spatial structures capable of governing specific interactions with DNA, RNA and proteins. The centromere is a specialized chromosomal structure that appears during cell division as a constricted central region where two chromatids are held together. In bioinformatic genome representations, centromeric DNA typically appears as mostly a string of N's near the end of each chromosome file; this is because centromeric DNA is difficult to sequence. Although variants placed in these N-string regions would be conspicuous, another strategy in accordance herewith is to place insertions or deletions in the regions flanking the centromere (e.g., within one sequence read length, or approximately 500 bp). These regions, in which sequencing read coverage overlaps with the centromere, are unusual and typically ignored, so adding watermark variants therein does not adversely affect legitimate analyses or the speed of the aligner.

Still another strategy is to exploit the nature of variants in a genome file, such as a Variant Call Format (VCF) file. A trio genotyping experiment may be performed, for example, in order to identify private variants (i.e., variants found in the child and neither of the parents can be assumed to be de novo variants) that can serve as a watermark. Such private variants can be assumed to be uncommon in the general population and thus useful as a watermark.

An alternative probabilistic approach exploits the fact that variants in a genome file (such as a VCF file including variants generated as a result of a whole genome sequencing analysis) can sometimes represent sequencing artifacts or other errors rather than true genetic variations. These variants are unattested and occur at a rate that suggests they are as likely to represent true genetic variation as they are likely to be errors. Knowledge of variant reliability, and accordingly, variants that are borderline reliable, can be utilized for watermarking purposes. For example, suppose there are a set of N variants in a genome file, each of which corresponds to a true variant with a probability or confidence level of 0.5 or less. This is sufficient to distinguish $2^N$ unique versions of the graph, one for each subset of the variants. Because these variants were previously unattested and, in some cases, a result of error, they should not be found in other graph references and can thus serve as a watermark. Although some practical challenges exist—internal dependencies among variants and reliabilities that can change over time for particular variants—the variant subsets may be used to index the graph versions and identify the origin of data extracted from them.

Figure 3:
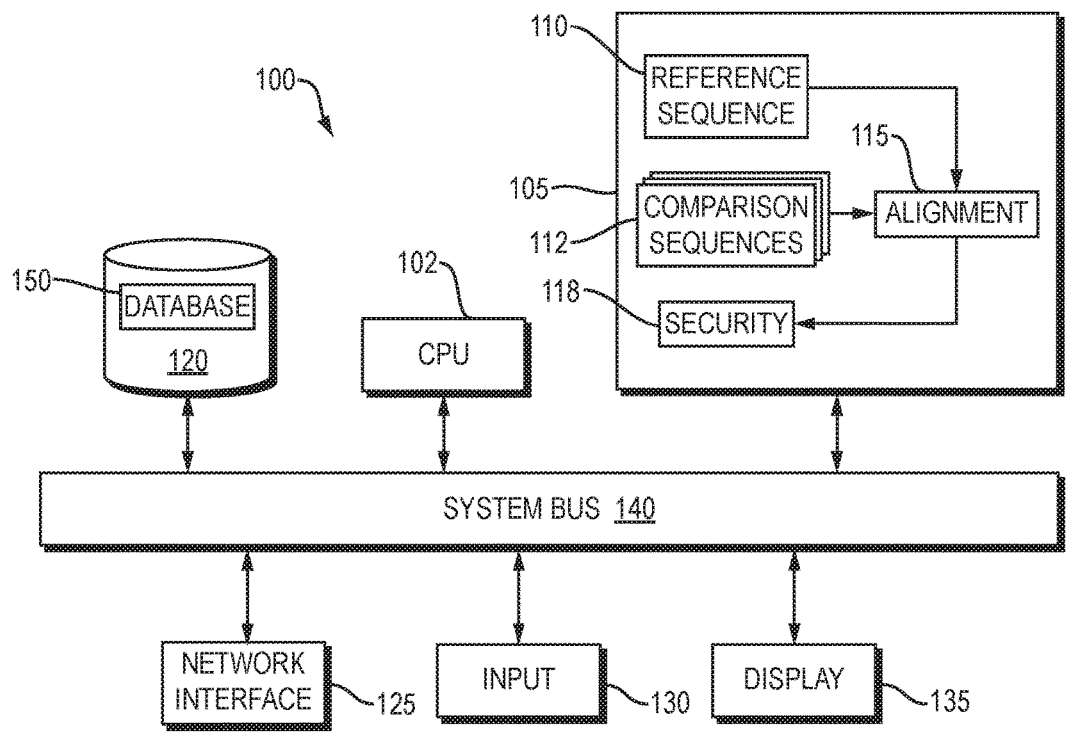
FIG. 3 is a block diagram of a representative computational architecture for implementing embodiments of the present invention.

The general approach taken by embodiments of the present invention is illustrated in FIG. 3, which illustrates, in block-diagram form, an exemplary computer 100 with features enabling it to align a received biological sequence and a stored biological reference sequence without compromising the reference sequence. The operation of computer 100 is directed by a central-processing unit ("CPU") 102. A main system memory 105, generally implemented as a bank of random-access memory (RAM), includes partitions for storing a nucleic-acid reference sequence 110, one or more received comparison sequences 112 each corresponding to a nucleic acid, an alignment module 115 (as described, for example, in the '226 patent) for identifying alignments between each comparison sequence and the reference sequence, and a security module 118. Security module 118 creates reference sequences 110 having watermarks as described herein.

More generally, main memory 105 contains instructions that control the operation of CPU 102 and its interaction with other hardware components. An operating system directs the execution of low-level, basic system functions such as memory allocation, file management and operation of one or more mass storage devices 120, typically one or more nonvolatile disk drives. A network interface 125 facilitates interaction with other computers and resources, permitting system 100 to receive comparison sequences and transmit alignments to customers. The computer 100 also includes input devices 130 (e.g., a keyboard, a mouse or other position-sensing device, etc.), by means of which a user can interact with the system, and a screen display 135. The computer 100 further includes a bidirectional system bus 140 over which the system components communicate, and as described in greater detail below, mass-storage device 120 may include one or more databases 150.

The distribution of functionality shown in FIG. 3 is representative only and intended to provide one possible topology. It is possible to distribute the functionality illustrated in FIG. 3 among more or fewer computational entities as desired, and components may intercommunicate over a computer network, e.g., a wired or wireless local-area network (LAN), wide-area network (WAN) and/or other types of networks. When used in a LAN networking environment, components may be connected to the LAN through a network interface or adapter. When used in a WAN networking environment, components typically include a modem or other communication mechanism. Modems may be internal or external, and may be connected to the system bus via the user-input interface, or other appropriate mechanism. Computers may be connected over the Internet, an Intranet, Extranet, Ethernet, or any other system that provides communications. Some suitable communications protocols may include TCP/IP, UDP, or OSI, for example. For wireless communications, communications protocols may include the cellular telecommunications infrastructure, WiFi or other 802.11 protocol, Bluetooth, Zigbee, IrDa or other suitable protocol. Furthermore, components of the system may communicate through a combination of wired or wireless paths.

Figure 4:
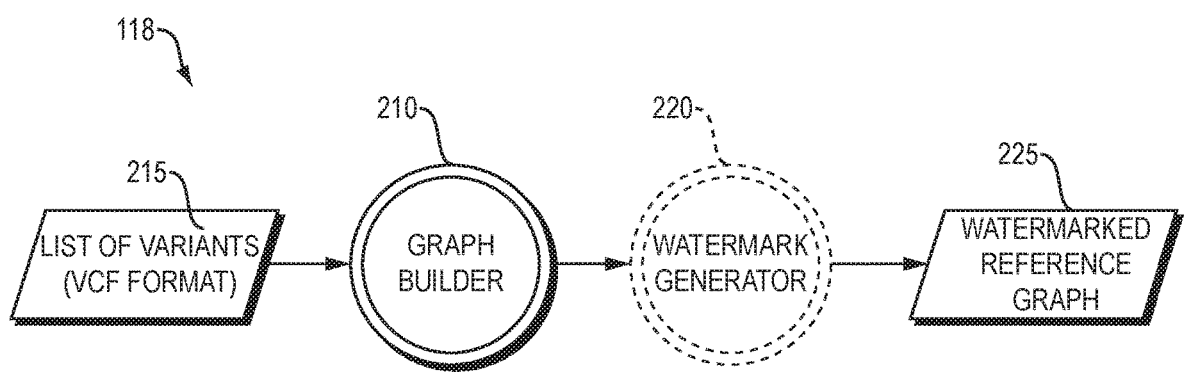
FIG. 4 is a block diagram showing in greater detail elements of a representative embodiment of the invention.

Components of a representative security module 118 are shown in FIG. 4. A graph builder 210 receives a genomic sequence including a list of variants 215 occurring in natural DNA, and creates a graph representation thereof—e.g., a directed acyclic graph including multiple paths reflecting the different variants. The graph builder 210 accepts input sequence data in, for example, VCF format, and the resulting graph is a reference that can be used to evaluate alignment with candidate sequences. In one embodiment, the graph builder 210 builds a graph iteratively by encoding each variant from a genetic sequence as an alternate path. To begin, a first edge is created as an object in a non-transitory memory (such as the memory 105) and associated with a genetic sequence, such as a portion of the human reference genome. Variation of that genetic sequence can be described by adding new edges to the graph to encode alternate paths including that variation. For example, the genetic sequence of a variant in a VCF file can be associated with a new edge and integrated into the graph such that the graph has two paths at the position containing the variation—one path follows the original reference, and the other includes the variant. To accommodate the new edge, the first edge is segmented into two at the position of the variation, and each of the edges are interconnected such that at the position of the variation one path follows the second edge, and the other follows the original orientation. Of course, a graph builder may associate genetic sequences with nodes rather than edges of the graph.

A watermark generator generates watermarks in accordance with one or more of the strategies discussed above and modifies the resulting graph—e.g., by adding new paths containing the watermarks—to produce a watermarked reference graph 225, which is stored in a partition in main system memory 105. The reference graph 225 may take the form of a computer-searchable data structure comprising at least one of (a) a plurality of insertions and deletions not found in natural genomic DNA, (b) a variant introduced in a repeat sequence other than the first of a plurality of repeat sequences in a repetitive region, (c) at least one sequence no longer than 30 bp not found in natural genomic DNA, or (d) metadata associated with variants in the reference graph.

Those skilled in the art will appreciate that the invention may be practiced with various computer system configurations, including multiprocessor systems, microprocessor-based or programmable consumer electronics, minicomputers, mainframe computers, and the like. The invention may also be practiced in distributed computing environments where tasks are performed by distributed processing devices linked through a communications network. In a distributed computing environment, program modules may be located in both local and remote computer-storage media including memory storage devices.

Any suitable programming language may be used to implement without undue experimentation the functions performed by the modules described herein. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript for example. Further, it is not necessary that a single type of instruction or programming language be utilized in conjunction with the operation of the system and method of the invention. Rather, any number of different programming languages may be utilized as is necessary or desirable.

CPU 102 may be a general-purpose processor, but may instead be or utilize any of a wide variety of other technologies including special-purpose hardware, a microcomputer, mini-computer, mainframe computer, programmed microprocessor, micro-controller, peripheral integrated circuit element, a CSIC (customer-specific integrated circuit), ASIC (application-specific integrated circuit), a logic circuit, a digital signal processor, a programmable logic device such as an FPGA (field-programmable gate array), PLD (programmable logic device), PLA (programmable logic array), smart chip, or any other device or arrangement of devices that is capable of implementing the functions of the invention as herein described.

While particular embodiments of the invention have been illustrated and described in detail herein, it should be understood that various changes and modifications might be made to the invention without departing from the scope and intent of the invention. From the foregoing it will be seen that this invention is one well adapted to attain all the ends and objects set forth above, together with other advantages, which are obvious and inherent to the system and method. It will be understood that certain features and sub-combinations are of utility and may be employed without reference to other features and sub-combinations. This is contemplated and within the scope of the appended claims.

The invention claimed is:

1. A system for modifying a deoxyribonucleic acid (DNA) sequence corresponding to a genome or portion thereof and represented as a reference graph, the system comprising:
 a memory partition for storing the sequence; and
 a watermarking module for modifying the sequence by introducing a watermarking artifact therein, the watermarking artifact comprising at least one of (a) a plurality of variants not found in natural genomic DNA, (b) a variant introduced in a repeat sequence other than the first of a plurality of repeat sequences in a repetitive region, (c) at least one sequence no longer than 30 bp not found in natural genomic DNA, or (d) metadata associated with variants in the reference graph, wherein the graph includes multiple paths at least one of which corresponds to a natural DNA sequence and another of which includes the watermarking artifact.

2. The system of claim 1, wherein the watermarking artifact is introduced in a region within 100 bp, 250 bp, or 500 bp of centromere DNA.

3. The system of claim 1, wherein the at least one variant is in a k-mer with k ranging from 15-30 bp.

4. The system of claim 1, wherein the metadata includes variant allele frequency information.

5. The system of claim 1, wherein a watermarking artifact comprises a frameshift in an essential gene.

6. The system of claim 1, wherein a watermarking artifact encodes an alternative protein sequence.

7. The system of claim 6, wherein the alternative protein sequence spells a word in a language.

8. The system of claim 1, wherein a variant introduced in a repeat sequence comprises a variant introduced in the middle of a repeat sequence.

9. The system of claim 1, wherein a variant not found in natural genomic DNA comprises a private variant found only in a single individual.

10. The system of claim 9, wherein the private variant is identified from a trio experiment.

11. A method of watermarking a deoxyribonucleic acid (DNA) sequence corresponding to a genome or portion thereof and represented as a reference graph and stored as a data structure in a computer memory, the method comprising modifying the memory contents corresponding to the sequence by introducing a watermarking artifact therein, the watermarking artifact comprising at least one of (a) a plurality of variants not found in natural genomic DNA, (b) a variant introduced in a repeat sequence other than the first of a plurality of repeat sequences in a repetitive region, (c) at least one sequence no longer than 30 bp not found in natural genomic DNA, or (d) metadata associated with variants in the reference graph, wherein the graph includes multiple paths at least one of which corresponds to a natural DNA sequence and another of which includes the watermarking artifact.

12. The method of claim 11, wherein the watermarking artifact is introduced in a region within 100 bp, 250 bp, or 500 bp of centromere DNA.

13. The method of claim 11, wherein the metadata includes variant allele frequency information.

14. The method of claim 11, wherein a watermarking artifact comprises a frameshift in an essential gene.

15. The method of claim 11, wherein a watermarking artifact encodes an alternative protein sequence.

16. The method of claim 11, wherein a variant introduced in a repeat sequence comprises a variant introduced in the middle of a repeat sequence.

17. The method of claim 11, wherein a variant not found in natural genomic DNA comprises a private variant found only in a single individual.

\* \* \* \* \*